United States Patent [19]
Kirby et al.

[11] Patent Number: 4,628,736
[45] Date of Patent: Dec. 16, 1986

[54] METHOD AND APPARATUS FOR MEASUREMENT OF ICE THICKNESS EMPLOYING ULTRA-SONIC PULSE ECHO TECHNIQUE

[75] Inventors: Mark S. Kirby, West Midlands, England; Robert J. Hansman, Jr., Scituate, Mass.

[73] Assignee: Massachusetts Institute of Technology, Cambridge, Mass.

[21] Appl. No.: 691,091

[22] Filed: Jan. 14, 1985

[51] Int. Cl.$^4$ ............................................. G01N 29/00
[52] U.S. Cl. ........................................ 73/590; 340/582
[58] Field of Search ........................ 73/590, 597, 629; 340/582, 580

[56] References Cited
U.S. PATENT DOCUMENTS

| | | | |
|---|---|---|---|
| 2,419,454 | 4/1947 | Le Clair | 340/582 |
| 4,388,830 | 6/1983 | Narushima et al. | 73/597 |
| 4,398,421 | 8/1983 | White | 73/597 |

Primary Examiner—Anthony V. Ciarlante
Attorney, Agent, or Firm—Sam Pasternack; James E. Maslow

[57] ABSTRACT

Method and apparatus for measurement of ice thickness employing ultra-sonic pulse echo technique, wherein an ultra-sonic pulse is emitted from a transducer at the ice-accreting surface of a structure, the pulse is reflected at the periphery of the accreted ice and the reflection is detected. The time delay is calibrated and related to ice thickness and accretion rate.

17 Claims, 3 Drawing Figures

PULSE-ECHO ICE ACCRETION MEASUREMENT- SYSTEM LAYOUT

PULSE-ECHO ICE ACCRETION MEASUREMENT-SYSTEM LAYOUT $$D = \frac{C_{ICE} T_{P-E}}{2}$$

ULTRASONIC PULSE-ECHO THICKNESS MEASUREMENT

# METHOD AND APPARATUS FOR MEASUREMENT OF ICE THICKNESS EMPLOYING ULTRA-SONIC PULSE ECHO TECHNIQUE

BACKGROUND OF THE INVENTION

The present invention relates to ice-prevention systems for aircraft structures, and more particularly, to an apparatus for measurement of ice thickness employing ultrasonic pulse echo techniques.

The problems relating to the formation of ice on aircraft structures are well known. In certain climatic conditions water droplets may exist at subfreezing temperatures in a liquid state. These supercooled droplets nucleate and form ice upon contact with the aircraft surfaces. Ice therefore tends to form on the leading edges of aircraft structures. The ice can degrade aircraft performance through increasing the effective weight of the aircraft and by increasing drag resistance and reducing lift provided by the airfoils.

Various ice detection devices are well known. In one known detection device, a probe is provided which extends beyond the surface to be monitored. However, the manner of ice accretion on such probe is different from the manner of ice accretion on the surface to be monitored. Hence, the accretion rate on the probe will be higher than the accretion rate on the surface to be monitored.

In another known device, the ice thickness is measured by the changing capacitance of a surface capacitor due to the dielectric properties of the ice which has accreted on the probe. One problem with this latter class of devices is that in order to accurately interpret the data received from the probe, the type of ice (rime, glaze, or mixed) must be known to the user.

It is therefore an object of the present invention to provide an apparatus for measurement of ice thickness which can be mounted flush with the surface upon which ice accretion thickness is to be measured.

It is another object of the present invention provide an apparatus for measurement of ice thickness which is insensitive to types of ice accreted.

It is yet another object of the present invention to provide an apparatus for measurement of ice thickness which is flush with the surface upon which ice accretion thickness is to be measured and can also measure the rate of ice accretion.

It is a further object of the present invention to provide an apparatus for measurement of ice thickness employing ultra-sonic pulse echo techniques to measure ice accretion thickness and also the rate at which ice is accreted.

SUMMARY OF THE INVENTION

The present invention relates to an apparatus for measurement of the thickness of accreted ice and rate of accretion employing an ultra-sonic pulse echo technique, comprising an ice-accreting surface and means mounted at said surface for transducing an ultra-sonic signal into said ice. The invention also relates to a method for detection of the presence of ice on a surface, comprising the steps of transmission of an ultra-sonic pulse into said ice via transducing means; propagation of said pulse through said ice to its periphery and reflection of said pulse back to said transducing means; and evaluating the time between transmission of said pulse and reception by said transducing means of said reflected pulse to obtain ice thickness, and/or ice accretion rate.

DESCRIPTION OF THE DRAWINGS

The preferred embodiment is illustrated in the accompanying drawings, in which.

DESCRIPTION OF THE PREFERRED EMBODIMENT

Figure 1:
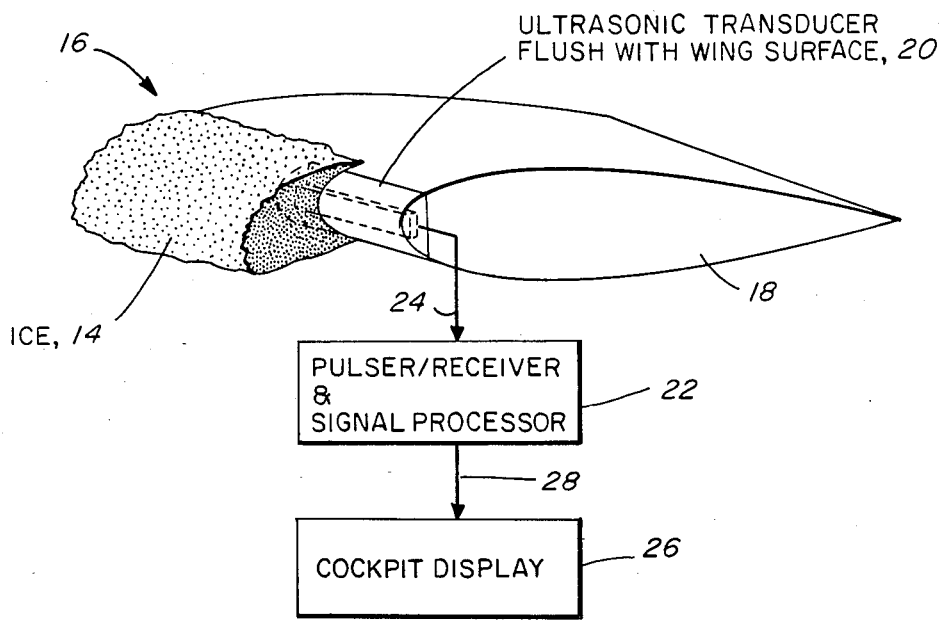
FIG. 1 is a partial schematic, partial block diagram of a preferred embodiment of the present invention.

FIG. 1 is a partial schematic, partial block diagram of the present invention, showing ice 14 accreted on the leading edge 16 of an airfoil 18. Also provided on the leading edge 16 of airfoil 18 is an ultra-sonic transducer 20.

In a preferred embodiment, the ultra-sonic sensor comprises a broad-band, highly damped contact transducer. This type of transducer allows maximum signal penetration in attenuating and scattering materials which have accreted thereon. Preferably, such transducer has a center frequency of 5 MHz and an element diameter of 0.25 inches. The transducer should at least have a center frequency of 1 to 20 MHz.

Referring again to FIG. 1, the transducer is driven by a pulse transmitter of a pulser/receiver and signal processor unit 22. The pulse transmitter transmits a signal to the transducer 20 via conductor 24. This signal causes the transducer to emit a brief ultrasonic compression wave. The emitted signal is reflected at the air-ice interface of the ice accreted on the transducer and the signal thus reflected back is detected by the transducer. This detected reflected wave is transmitted from the transducer back to the pulser/receiver and signal processor unit 22 by means of conductor 24. The received signal is then processed by the signal processor within unit 22 and a signal is thereafter conducted to a display device 26 by means of a cable 28.

Figure 2:
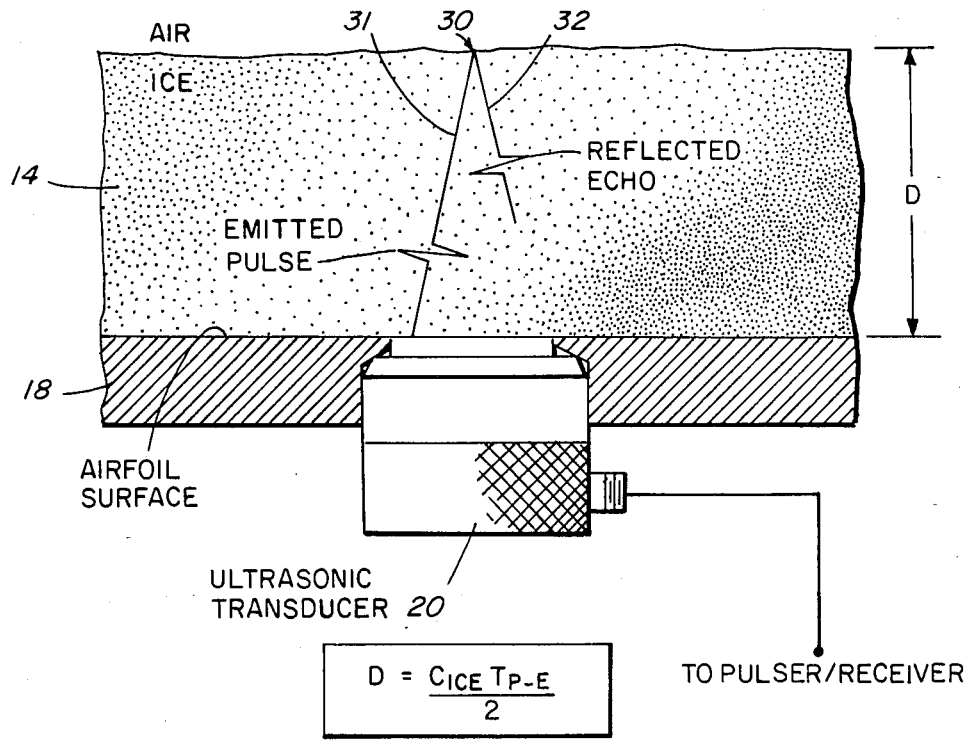
FIG. 2 is a schematic diagram illustrating the pulse echo technique of ice thickness measurement.

As will be appreciated by those of ordinary skill in the art, the principle upon which the pulse echo feature of the invention operates, is shown in the schematic diagram of FIG. 2. In FIG. 2, a transducer 20 is shown mounted flush with the surface of airfoil 18. As will be seen in the figure, a pulse 31 is emitted by the transducer and is propagated through the ice 14 until it is reflected by the air-ice interface 30. The echo 32 is detected by the transducer 20, whereupon an electrical pulse, representative of the strength of the echo, is transmitted to the receiver of unit 22. The time delay between the emission of the pulse by the transducer and its receipt of the reflected pulse 32 is related to the thickness of the ice. This relationship is shown in FIG. 2 in the block enclosing the formula D (ice thickness)=$\frac{1}{2}$ of the quantity $C_{ice}$ (representing the speed of sound in ice)$\times T_{p-E}$ (which represents the time between the emission of the pulse and the receipt of the echo). It will therefore be appreciated that ice thickness D can be detected if the time of propagation can be detected and the speed of sound in the ice is known.

Furthermore, the inventors have determined that the speed of sound $C_{ice}$ in ice is insensitive to the type of ice under examination. This speed has been determined experimentally to be approximately 3.8 mm/microseconds.

Figure 3:
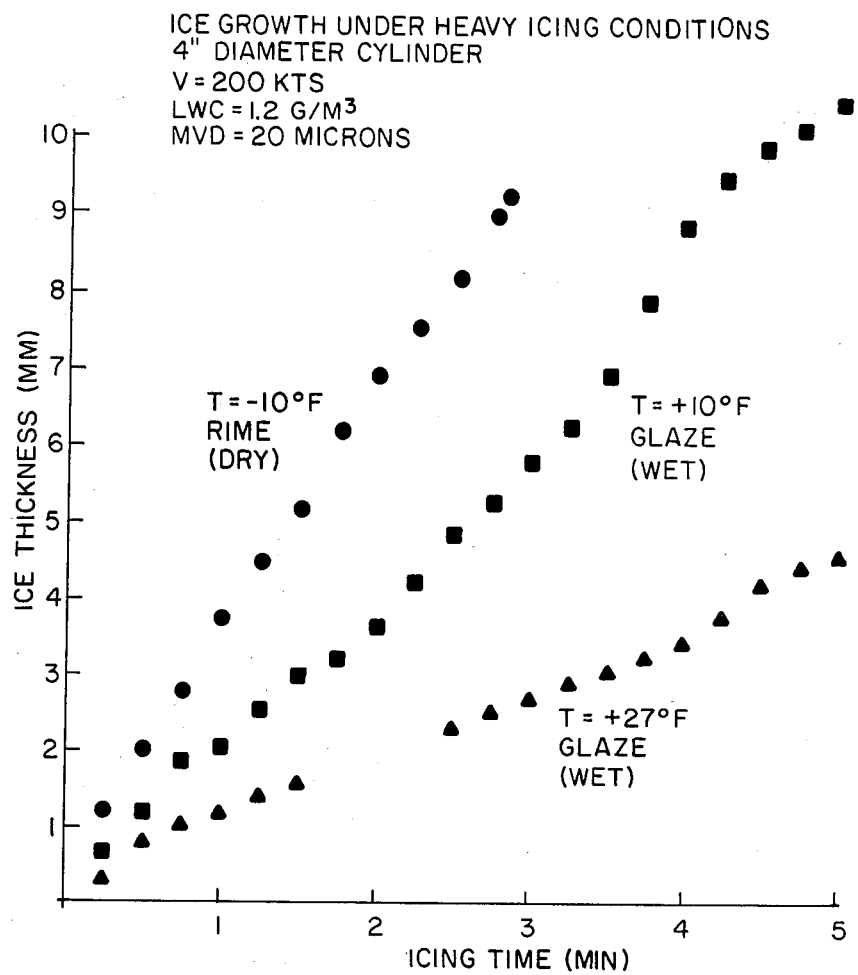
FIG. 3 is a graphic representation of experimental data representing ice growth under heavy icing conditions for detection of ice thickness and growth rate.

Referring to FIG. 3, there is shown a graphic representation of experimental data representing ice growth under heavy icing conditions employing a 4-inch diameter cylinder with the present apparatus flush mounted at the leading edge thereof. The detectors were subjected to an icing cloud at 200 knots. The cloud had a median volume diameter of 20 microns and a liquid water content of 1.2 grams per meter cubed. Three temperatures ($-10°$ F., $+10°$ F., $+27°$ F., respectively) representing three types of ice formation (rime, glaze and a second glaze, respectively) are shown. The graph of FIG. 3 compares ice thickness in millimeters along the ordinate axis to icing time in minutes along the abscissa axis. The icing rate for each respective formation is represented by the slope of the respective point-plotted curve shown in the figure.

It will be appreciated that the present apparatus for measurement of ice thickness can be advantageously used in conjunction with ice de-icing and anti-icing-devices to protect a vehicle from unwanted icing. This is particularly critical in operation of pneumatic boots, which are only effective within an certain limited ice thickness range. Therefore, knowledge of ice thickness and ice growth rate is critical for efficient operation of such device.

While rather specific embodiments have been described herein, it will be appreciated that other and further embodiments within the spirit and scope of the present invention are contemplated.

We claim:

1. An apparatus for measurement of the thickness of ice on an ice-accreting surface employing an ultra-sonic pulse echo technique, comprising:
   an ice-accreting surface;
   transducer means mounted at said surface for transmitting an ultra-sonic signal into said ice and for receiving a reflected signal; and
   means for evaluating the time delay between transmission and reception of the ultra-sonic signal, the time delay indicative of the thickness of the ice.

2. The apparatus of claim 1, wherein said transducer means comprises at least one transducer mounted flush at said surface.

3. The apparatus of claim 1, wherein said transducer is mounted behind said surface.

4. The apparatus of claim 1, wherein said transducer is mounted on said surface.

5. The apparatus of claim 1, further comprising a pulse transmitter and receiver operatively coupled to said transducing means.

6. The apparatus of claim 1, further comprising a signal processor operatively coupled to said transducing means.

7. The apparatus of claim 1, further comprising a display operatively coupled to said transducing means.

8. The apparatus of claim 7, wherein said display comprises means for indicating ice thickness and accretion rate.

9. The apparatus of claim 7, wherein said display comprises an ice warning indicator.

10. The apparatus of claim 1, wherein said transducing means comprises a broadband, highly damped contact transducer.

11. The apparatus of claim 10, wherein said transducing means has a center frequency range of 1–20 MHz.

12. The apparatus of claim 11, wherein said center frequency is approximately 5 MHz.

13. The apparatus of claim 1, wherein said transducing means comprises a piezo electric element.

14. The apparatus of claim 13, wherein said element has a diameter of approximately 0.25 inches.

15. A method for detection of the presence of ice on a surface, comprising the steps of:
   (a) transmission of an ultra-sonic pulse into said ice via transducing means mounted at said surface;
   (b) propagation of said pulse through said ice to its periphery and reflection of said pulse back to said transducing means; and
   (c) evaluating the time between transmission of said pulse and reception by said transducing means of said reflected pulse to obtain ice thickness.

16. A method for detection of the presence of ice on a surface, comprising the steps of:
   (a) transmission of an ultra-sonic pulse into said ice via transducing means mounted at said surface;
   (b) propagation of said pulse through said ice to its periphery and reflection of said pulse back to said transducing means; and
   (c) evaluating the time between transmission of said pulse and reception by said transducing means of said reflected pulse to obtain ice accretion rate.

17. A method for controlling ice protection devices comprising the steps of determining the presence and thickness of ice on a surface protected by said protection devices, by means of ultra-sonic pulse echo detection according to claim 16, and directing said devices to protectively operate.

* * * * *